United States Patent [19]

Wentler et al.

[11] 4,301,044

[45] Nov. 17, 1981

[54] BIODEGRADABLE ZWITTERIONIC SURFACTANT COMPOUNDS

[75] Inventors: George E. Wentler, Middletown; Joseph McGrady, Cincinnati; Eugene P. Gosselink, Cincinnati; William A. Cilley, Cincinnati, all of Ohio

[73] Assignee: The Procter & Gamble Company, Cincinnati, Ohio

[21] Appl. No.: 114,184

[22] Filed: Jan. 22, 1980

[51] Int. Cl.$^3$ ........................ C11D 3/066; C11D 1/18; C07C 141/02

[52] U.S. Cl. .................................... 252/545; 560/156; 560/179; 252/544; 560/180; 560/186; 252/546; 560/188; 560/189; 252/547; 252/549; 260/401; 260/404; 260/458 R; 260/458 C; 548/354; 560/20; 560/23; 560/37; 560/45; 560/50; 560/60; 560/64; 560/74; 560/81; 560/84; 560/89; 560/90; 560/91; 560/103; 560/105; 560/110; 560/112; 560/130; 560/138; 560/142; 560/144; 560/145; 560/146

[58] Field of Search ............... 260/400, 401, 403, 404, 260/404.5 R, 458 R, 458 C; 548/354; 252/DIG. 6, 542, 544, 545, 546, 547, 549, 551, 174.16; 560/20, 23, 37, 45, 50, 60, 64, 74, 81, 84, 89, 90, 91, 103, 105, 110, 112, 130, 144, 145, 146, 156, 179, 180, 186, 188, 189

[56] References Cited

U.S. PATENT DOCUMENTS

| | | | |
|---|---|---|---|
| 3,113,026 | 12/1963 | Sprung | 96/107 |
| 3,497,482 | 2/1970 | Hwa | 260/79.3 |
| 3,562,170 | 2/1971 | Zorayan et al. | 260/401 |
| 3,684,427 | 8/1972 | Walz | 8/26 |
| 3,843,707 | 10/1974 | Danzik et al. | 260/458 R |
| 3,896,034 | 7/1975 | Eckert | 252/547 |
| 3,925,262 | 12/1975 | Laughlin et al. | 252/526 |
| 3,929,678 | 12/1975 | Laughlin et al. | 252/526 |
| 4,000,091 | 12/1976 | Wentler | 252/524 |
| 4,000,092 | 12/1976 | Wentler | 252/526 |
| 4,159,277 | 6/1979 | Gosselink et al. | 260/458 R |
| 4,165,334 | 8/1979 | Gosselink et al. | 260/458 R |
| 4,204,065 | 5/1980 | Bodor | 546/316 |

FOREIGN PATENT DOCUMENTS

| | | |
|---|---|---|
| 1034296 | 6/1966 | United Kingdom . |
| 1302794 | 1/1973 | United Kingdom . |

OTHER PUBLICATIONS

Smith et al., JAOCS 53, 69 (1976).

*Primary Examiner*—John F. Niebling
*Attorney, Agent, or Firm*—Donald E. Hasse; Steven J. Goldstein; Robert B. Aylor

[57] ABSTRACT

Zwitterionic surfactant compounds are made readily biodegradable in the environment by the inclusion of a biochemically and/or hydrolytically labile chemical linkage located between the cationic and anionic charge centers of the compounds and anywhere from the second to the tenth atom distant from the cationic charge center. The biodegradable linkage is preferably an ester or amide. The alkoxylated zwitterionic surfactants herein exhibit outstanding particulate soil removal performance and are also effective in removing oily soils from fabrics, in addition to being readily biodegradable. Also described are detergent compositions containing the zwitterionic surfactants, and, optionally containing cosurfactants and detergent builders.

19 Claims, No Drawings

BIODEGRADABLE ZWITTERIONIC SURFACTANT COMPOUNDS

TECHNICAL FIELD

This invention relates to zwitterionic surfactant compounds, and detergent compositions containing them, which exhibit both outstanding particulate soil removal performance and a high degree of biodegradability in the environment due to the inclusion of a biodegradable linkage, preferably an ester or amide, between the cationic and anionic charge centers of the compounds.

BACKGROUND ART

Zwitterionic surfactants, i.e., those surface active compounds that contain both positive and negative charge centers in the same molecule while being electrically neutral, are well known and have been used in fabric laundering operations. Zwitterionic surfactants having alkylene oxide groups, and detergent compositions containing them, are also known. For example, U.S. Pat. No. 3,925,262 issued to Laughlin et al. on Dec. 9, 1975, discloses detergent compositions, which exhibit improved particulate soil removal performance, containing certain ethoxylated zwitterionic surfactants together with conventional detergent builder materials. Similarly, U.S. Pat. No. 3,929,678 issued to Laughlin et. al. on Dec. 30, 1975, discloses detergent compositions containing ethoxylated zwitterionic surfactants together with various cosurfactants for enhanced particulate soil removal. Zwitterionic surfactant compounds with a tetramethylene oxide moiety between the charge centers are disclosed in U.S. Pat. No. 4,159,277 issued to Gosselink et. al. on June 26, 1979. These compounds are combined with cosurfactants and builders, respectively, in U.S. Pat. No. 4,000,091 and U.S. Pat. No. 4,000,092, both issued to Wentler on Dec. 28, 1976. The pending application of Laughlin et. al. U.S. Ser. No. 849,745, filed Nov. 9, 1977 discloses certain zwitterionic compounds with alkyleneoxy groups for enhanced cleaning performance. Finally, U.S. Pat. No. 4,165,334, issued to Gosselink et. al. on Aug. 21, 1979 discloses ethoxylated sulfonium zwitterionic compounds and detergent compositions containing them. All of the above patents and the pending application are incorporated herein by reference.

While the zwitterionic surfactants disclosed above provide outstanding particulate soil removal performance, some even in the absence of builder materials, it would be desirable to improve their biodegradability in the environment. The present invention incorporates certain biodegradable chemical linkages between the cationic and anionic charge centers of alkyleneoxy zwitterionic compounds to make them readily biodegradable. It is to be understood that the placement of the linkage between the charge centers and anywhere from the second to the tenth atom from the cationic charge center is necessary to achieve the biodegradation advantages over compounds known in the prior art. Thus the compounds of the present invention provide both outstanding particulate soil removal performance and a high degree of biodegradability, and are therefore especially suitable for use in detergent compositions.

SUMMARY OF THE INVENTION

The present invention encompasses compounds of the formula $$M-(R^4)-(A)_m-(R^5)_n-(CHR^6)_n-(O)_n-(R^7O)_y-(R^5)-X$$

wherein M is selected from the group consisting of

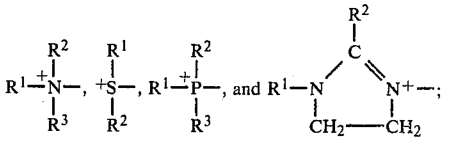

$R^1$ is selected from the group consisting of straight chain, branched chain or cyclic $C_1$–$C_{30}$ alkyl, hydroxyalkyl, alkenyl and hydroxyalkenyl moieties and alkaryl moieties in which the alkyl group has 6–24 carbon atoms; $R^2$ and $R^3$ are each selected from the group consisting of straight chain, branched chain or cyclic $C_1$–$C_{30}$ alkyl, hydroxyalkyl, alkenyl and hydroxyalkenyl moieties, alkaryl moieties in which the alkyl group has 6–24 carbon atoms, and $C_2$–$C_4$ alkylene oxide having from 1 to 5 alkyleneoxy units; or wherein two of the above R groups are joined to form a $C_4$–$C_6$ heteroring with the nitrogen or phosphorus atom; $R^4$ is an alkylene, hydroxyalkylene, alkylene oxide, alkenylene, arylene, or alkarylene group, provided that A is no more than 10 atoms from M; each A is selected from the group consisting of

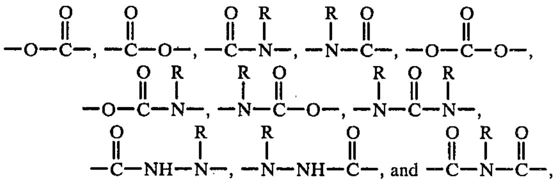

wherein R is hydrogen or a $C_1$–$C_5$ alkyl or hydroxyalkyl group; m is 1 or 2, but can only be 2 when an additional $R^5$ group separates the A structure; $R^5$ is a $C_1$–$C_{10}$ alkylene, hydroxyalkylene, alkenylene, arylene, or alkarylene group; each n is independently 0 or 1; $R^6$ is selected from the group consisting of straight chain, branched chain or cyclic $C_1$–$C_{30}$ alkyl, hydroxyalkyl, alkenyl and hydroxyalkenyl moieties and alkaryl moieties in which the alkyl group has 6–24 carbon atoms; $R^7$ is a $C_2$–$C_4$ alkylene group or mixtures thereof; y is from 3 to 100; and X is sulfate, sulfonate or carboxylate; provided that the above groups are selected such that $R^1$, $R^2$, $R^3$ and $R^6$, together, contain from 12 to 50 carbon atoms and no peroxy linkages are present in the compound.

The above-described zwitterionic surfactant compounds are readily biodegradable in the environment and provide excellent particulate soil removal from laundered fabrics, even in the absence of conventional builder materials. Moreover, the compounds of this type are effective for removing oily soil. These compounds can be incorporated in detergent compositions, which optionally can contain various cosurfactants and detergent builders for enhanced performance.

DETAILED DESCRIPTION OF THE INVENTION

This invention relates to the discovery that zwitterionic surfactant compounds can be made readily biodegradable in the environment by the inclusion of a biochemically and/or hydrolytically labile linkage between the cationic and anionic charge centers of the compounds. These zwitterionic compounds exhibit excellent biodegradability since they can be cleaved at the linkage, producing two lower molecular weight species which are quite readily degraded in the environment.

In its broadest aspect, the present invention encompasses zwitterionic compounds comprising molecules made up of five distinct parts. Referring to the foregoing formula, the compounds herein comprise a cationic charge center, M; a lipophilic hydrocarbon portion, composed of groups $R^1$, $R^2$, $R^3$ and $R^6$; an anionic charge center, X; an alkylene oxide moiety interposed between the cationic and anionic charge centers; and a biodegradable linkage also interposed between the charge centers and located anywhere from the second to the tenth atom distant from the cationic charge center. The biodegradable linkage is preferably located from the second to the sixth atom from the cationic charge center for optimum biodegradability.

The biodegradable linkage for use in the present invention is selected from the group consisting of:

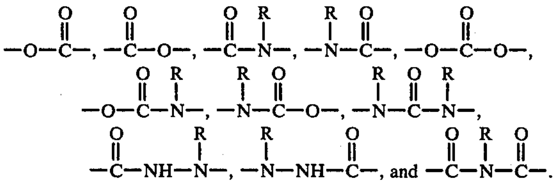

Preferably the linkage is selected from the group consisting of

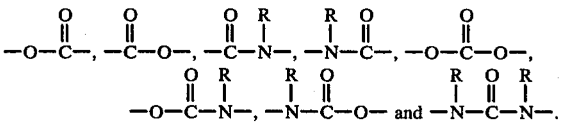

Most preferably, the linkage is

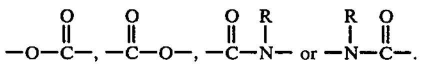

In the above structures, R is hydrogen or a $C_1$-$C_5$ alkyl or hydroxyalkyl group. It is preferred, for ease of formulation, that there only be one biodegradable linkage in the compounds of this invention. However, there may optionally be two such linkages provided there is sufficient connecting structure between the linkages to make them stable for their intended use, i.e. in detergent compositions. Thus, in the general formula for the compounds of the invention, m can be 2 only when additional $R^5$ group separates the A structures.

The cationic charge center, M, of the present zwitterionic compounds is selected from the group consisting of

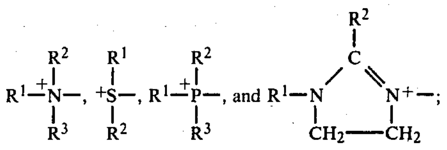

and is preferably

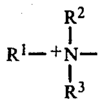

due to the availability of amine precursor compounds.

In the above structures, $R^1$ is selected from the group consisting of straight chain, branched chain or cyclic $C_1$-$C_{30}$ alkyl, hydroxyalkyl, alkenyl and hydroxyalkenyl moieties and alkaryl moieties in which the alkyl group has 6-24 carbon atoms; $R^2$ and $R^3$ are each selected from the group consisting of straight chain, branched chain or cyclic $C_1$-$C_{30}$ alkyl, hydroxyalkyl, alkenyl and hydroxyalkenyl moieties, alkaryl moieties in which the alkyl group has 6-24 carbon atoms, and $C_2$-$C_4$ alkylene oxide having from 1 to 5 alkyleneoxy units; or wherein two of the above R groups are joined to form a $C_4$-$C_6$ heteroring with the nitrogen or phosphorus atom. Simple heteroring structures involving the nitrogen atom are e.g., morpholine, piperidine, pyridine, etc. These ternary amines can be quaternized in the same way as a trialkyl teritary amine.

When preparing a detersive surfactant of the present type, it will be recognized that the $R^1$, $R^2$, and $R^3$ groups located on the cationic charge center, M, and the $R^6$ group (which is selected from the group consisting of straight chain, branched chain or cyclic $C_1$-$C_{30}$ alkyl, hydroxyalkyl, alkenyl and hydroxyalkenyl moieties and alkaryl moieties in which the alkyl group has 6-24 carbon atoms) located between the charge centers should be selected to provide sufficient hydrocarbon content that the hydrocarbon portion of the molecule has substantial hydrophobic lipophilic character. However, the total hydrocarbon content should not be so great that the molecule is rendered insoluble. Thus $R^1$, $R^2$, $R^3$, and $R^6$ should, together, contain from about 12 to 50 carbon atoms, preferably from about 15 to 30 carbon atoms. In general, it can be stated that where there is a higher degree of hydrocarbon content provided by the $R^6$ group, useful compounds can be obtained when $R^1$, $R^2$ and $R^3$ have less hydrocarbon content.

In one class of preferred zwitterionic compounds herein, the hydrocarbon content is primarily provided by the $R^1$, $R^2$ and $R^3$ groups located on the cationic charge center. These comounds are obtained when, in the general formula for the compounds, the n subscript for the ($CHR^6$) group is zero, or if this n is 1, then $R^6$ should be a short carbon-chain group, for instance a $C_1$-$C_4$ alkyl, alkenyl or hydroxy-substituted alkyl or alkenyl group. In this class of compounds, $R^1+R^2+R^3$ should, together, contain at least about 12 carbon atoms, more preferably at least about 14 carbon atoms.

Based on the foregoing considerations regarding the total hydrocarbon content of the groups $R^1+R^2+R^3$ for the above class of compounds, it will be recognized by those skilled in the detergency arts that the hydrophobic character for good detergency performance is secured when, for example, group $R^1$ is a straight chain or branched chain $C_{10}$–$C_{30}$ alkyl or alkenyl moiety, or an alkaryl moiety having a $C_6$–$C_{24}$ alkyl group, and $R^2$ and $R^3$ are each independently selected from $C_1$–$C_4$ alkyl, alkenyl or hydroxy-substituted alkyl or alkenyl moieties. Preferably $R^1$ is a $C_{14}$–$C_{22}$ alkyl moiety or alkaryl moiety having a $C_8$–$C_{16}$ alkyl group; more preferably $R^1$ is a $C_{14}$–$C_{20}$ alkyl moiety. Preferably $R^2$ and $R^3$ are each independently selected from $C_1$–$C_3$ alkyl moieties, especially methyl.

Compounds wherein groups $R^1$ and $R^2$ are each independently selected from $C_6$–$C_{22}$ alkyl or alkenyl moieties and alkaryl moieties having a $C_6$–$C_{16}$ alkyl group, and wherein $R^3$ is a $C_1$–$C_4$ alkyl, alkenyl or hydroxy-substituted alkyl or alkenyl moiety, also have sufficient hydrocarbon content that the molecule has substantial hydrophobic character; accordingly, these are also highly useful detersive surfactants. Preferably, $R^1$ and $R^2$ are each independently selected from $C_8$–$C_{16}$ alkyl moieties (most preferably from $C_{10}$–$C_{14}$ alkyl moieties) and $R^3$ is a $C_1$–$C_3$ alkyl, especially methyl group. The sum of $R^1+R^2+R^3$ carbon atoms should be in the range from 12 to about 50, preferably from 14 to about 40.

Compounds wherein $R^1$, $R^2$ and $R^3$ are each independently selected from $C_6$–$C_{16}$ alkyl or alkenyl moieties and alkaryl moieties having a $C_6$–$C_{10}$ alkyl group are also useful detersive surfactants. Preferably $R^1$, $R^2$ and $R^3$ are each independently selected from $C_8$–$C_{16}$ alkyl moieties, more preferably from $C_8$–$C_{12}$ alkyl groups. The sum of $R^1+R^2+R^3$ carbon atoms should be in the range from about 18 to about 48, preferably about 24 to about 36.

In another class of preferred zwitterionic compounds herein, the hydrocarbon content is primarily provided by the $R^6$ hydrocarbon group located between the charge centers. These compounds are obtained when, in the general formula, $R^6$ is a straight chain or branched chain $C_{10}$–$C_{30}$ alkyl or alkenyl moiety or an alkaryl moiety having a $C_6$–$C_{24}$ alkyl group, the n subscript for the $(CHR^6)$ group is one, and $R^1$, $R^2$ and $R^3$ are each independently short carbon-chain groups, for instance $C_1$–$C_4$ alkyl, alkenyl or hydroxy-substituted alkyl or alkenyl moieties. In this class of compounds, $R^6$ is preferably a $C_{14}$–$C_{22}$ alkyl moiety or alkaryl moiety having $C_8$–$C_{16}$ alkyl group, more preferably $R^6$ is a $C_{14}$–$C_{22}$ alkyl moiety, and $R^1$, $R^2$ and $R^3$ are preferably each independently selected from $C_1$–$C_3$ alkyl moieties, most preferably $R^1$, $R^2$ and $R^3$ are all methyl groups.

The anionic charge center, X, is sulfate, sulfonate or carboxylate, and is preferably sulfate or sulfonate for ease of manufacture and detergency performance. These negatively charged hydrophilic moieties are well recognized in the detergency arts as useful for imparting water solubility to detersive surfactants.

The zwitterionic compounds herein must contain at least three alkyleneoxy groups between the biodegradable linkage A and the anionic charge center X to deliver good particulate soil removal performance. Thus, referring to the general formula for the compounds herein, $R^7$ is a $C_2$–$C_4$ alkylene group, or mixture thereof, and y is anywhere from 3 to 100. Preferably, $R^7$ is ethylene and y is from 3 to 30, more preferably from 6 to 12.

It will be understood that the numbers recited herein for alkylene oxide content may refer either to single compounds having, for example, 9 units of alkylene oxide per molecule, or to compound mixtures in which the average degree of alkoxylation is equal to, for example, 9 units of alkylene oxide per molecule. Commercial processes for preparing polyalkylene oxide chains normally result in mixtures of compounds having a distribution of polyalkylene oxide chain lengths.

The compounds of this invention also contain various connecting groups, which are designated as $R^4$ and $R^5$ in the general formula for the compounds herein. $R^4$ can be, for example, an alkylene, hydroxyalkylene, alkylene oxide, alkenylene, arylene, or alkarylene group. However, $R^4$ must be selected such that the linkage A is no more than 10 atoms from the cationic charge center M. Each $R^5$ can be, for example, a $C_1$–$C_{10}$ alkylene, hydroxyalkylene, alkenylene, arylene, or alkarylene group. The compounds herein may also contain an oxygen atom, for ease of synthesis of certain compounds, located immediately before the $(R^7O)_y$ group in the general formula for the compounds herein. Further, each n in the general formula for the compounds herein is independently 0 or 1.

In preparing compounds as described above, it will be recognized that the components must be selected to form stable compounds. Thus, peroxy linkages are to be avoided, and as a general rule, two or more carbon atoms are needed between heteroatoms for chemical stability. More particularly, $R^4$ must be a $C_2$ or higher group for a stable linkage of M to a nitrogen or oxygen atom in the A linkages. However, $R^4$ must not be a $C_2$ group for a linkage of M to a carbonyl group in the A linkages since a propionate moiety at the cationic charge center is chemically unstable. Similarly, where X is a carboxylate anion, it is preferred that the $R^5$ group preceding it not be a $C_2$ group since a propionate moiety at the anionic center is also relatively unstable. The range of selection of this $R^5$ group is somewhat less critical than the other R groups, and is usually dictated merely on the basis of the synthesis scheme used to prepare the compounds of choice. Of course, if this $R^5$ group is too long, water solubility of the compounds can be adversely affected. Conveniently, this $R^5$ can be a $C_1$–$C_4$ alkylene, a $C_3$–$C_4$ hydroxy-substituted alkylene, or a phenylene group. Most preferably, $R^5$ is ethylene except that, as noted above, when the group A is COO—, it is most preferably methylene.

In the context of the present invention, zwitterionic compounds having hydroxy substituents on the carbon atoms immediately adjacent the M and/or X moiety are not preferred, since they are unstable in water, especially at pH's other than neutrality, and are extremely difficult to prepare compared with other hydroxy substituted compounds.

A group of particularly preferred compounds of the present invention have the formula

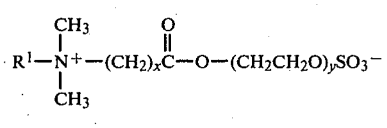

wherein $R^1$ is a $C_{14}$–$C_{20}$ alkyl group, x is 1 or an integer from 3 to 5 and y is from 6 to 12. An especially preferred compound of the foregoing type is one in which $R^1$ is a $C_{16}$ alkyl group, x is 1 and y is 9.

Other particularly preferred compounds include those of the formula

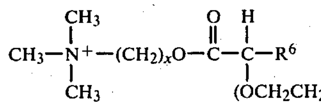

wherein $R^6$ is a $C_{14}$–$C_{20}$ alkyl group, x is an integer from 2 to 5 and y is from 6 to 12. An especially preferred compound is one in which $R^6$ is a $C_{16}$ alkyl group, x is 2 and y is 9.

The synthesis of the zwitterionic surfactant compounds herein is carried out using commercially available starting materials and known chemical reaction steps. For example, synthetic methods for the preparation of various ethoxylated zwitterionic surfactant compounds are described in U.S. Pat. No. 3,929,678, Laughlin et al., particularly from Column 6 through Column 11, line 51. U.S. Pat. No. 4,159,277, Gosselink et al., describes the preparation of zwitterionic surfactant compounds containing tetramethylene oxide moieties from Column 5, line 19 to Column 11, line 4. The synthesis of zwitterionic compounds containing various alkyleneoxy groups between the charge centers is described in the pending application of Laughlin et al., U.S. Ser. No. 849,745. Finally, U.S. Pat. No. 4,165,334 describes the synthesis of sulfonium zwitterionic compounds in Column 5, lines 5 through 55, and from Example I in Column 14 through Column 18, line 20.

A non-limiting example of a general synthetic route for the preparation of a preferred compound herein is as follows.

Step I: Preparation of Mono Chloroacetyl Derivative of PEG

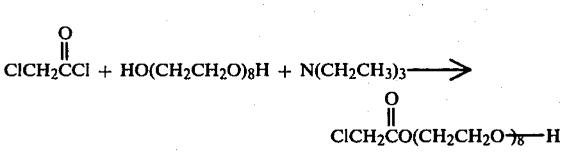

A mixture of 200 g (0.5 mole) of commercial polyethylene glycol (PEG 400), 50.5 g (0.5 mole) triethylamine, and 1L chloroform was added to a 3-neck flask and cooled to 0° C. in an ice-salt bath. Chloroacetyl chloride (56.5 g., 0.5 mole) was added over a 4 hr. period to the stirred mixture via a dropping funnel while maintaining the reaction temperature at 0°–5° C. The crude reaction product was washed successively with 1000 ml of a 2.5% aqueous solution of NaCl, 750 ml 10% HCl solution which contained 25 g NaCl, and finally 1000 ml 2.5% NaCl solution. After drying over $Na_2SO_4$ and removing the solvent via rotovaporation, 171 gm liquid was obtained. The brownish liquid was purified via column chromatography (100–200 mesh silica gel H) using as solvent a 99:1 mixture of methyl ethyl ketone and water. Infrared and nuclear magnetic resonance spectroscopy confirmed the structure.

Step II: Quaternization of Chloroacetyl PEG

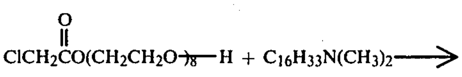

-continued

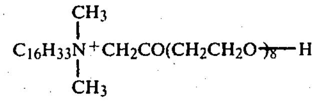

A mixture of the chloroacetyl PEG (13.6 g, 30 mmole), dimethylhexadecylamine (8.3 g, 30 mmole), and 60 ml acetonitrile was stirred and heated at reflux for 8 hours. The acetonitrile was removed by flash evaporation and the crude residue triturated three times with hexane to remove unreacted amine and ester. The remaining dark brown product was sulfated without further purification. The NMR spectra were consistent with the structure.

Step III: Sulfonation of Quaternized Chloracetyl PEG

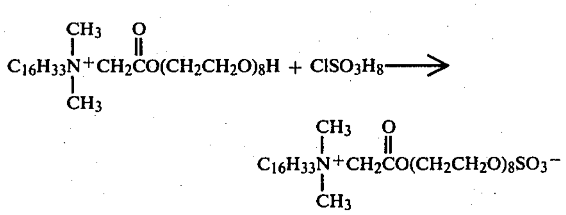

A mixture of 18 gm (25 mmole) of the quaternary compound and 60 ml $CHCl_3$ was cooled to 0°–5° C. in a 3-neck round bottom flask. 3.1 ml chlorosulfonic acid in 7 ml $CHCl_3$ was added, via a dropping funnel, to the stirred mixture. Stirring at 0°–5° C. was continued for an additional 30 mins., after which time the cooling bath was removed and the mixture allowed to warm to room temperature over a 1½ hour period. The crude reaction mix was washed 4 times with 5% NaCl solution. The $CHCl_3$ layer containing the product was stirred with 100 g Rexyn 300 $H^+OH$ mixed bed ion-exchange resin which had previously been rinsed with water, methanol, and finally chloroform. After about 45 minutes, the mixture was filtered and the filtrate treated with 100 g of fresh resin for an additional 45 minutes. Filtration and evaporation of solvent gave the final product.

A non-limiting example for the preparation of another preferred compound of the present invention is as follows.

Step I: Preparation of Alpha-Ethoxylated Stearic Acid 501.6 g of pre-dried (molecular sieves) polyethylene glycol (average mo. wt. 380–420) was added, under a nitrogen blanket to a 2 liter, 5 neck round bottom flask, equipped with reflux condenser, mechanical stirrer and heating mantle. Toluene (700 ml) was added and the mixture heated to reflux (about 110° C.). Metallic sodium (19.8 g, 0.862 moles) was added portionwise over a period of one hour. Following addition of the sodium, the mixture was stirred at reflux for an additional one half hour followed by the addition of 100 g (0.313 moles) of alpha-chlorostearic acid in 150 ml of distilled toluene.

The reaction mixture was allowed to stir at reflux for two hours, then cooled to room temperature. Upon standing at room temperature, the reaction mixture separated into two phases. The upper, organic phase was distilled under reduced pressure to remove toluene and the residue recombined with the lower phase, cooled to 0°–10° C., and the pH adjusted to pH2 with concentrated HCl.

The acidic solution was extracted with an equal volume of ethyl acetate and the acetate extracts washed several times with a saturated NaCl solution. The ethyl acetate was removed under reduced pressure and the residue dissolved in chloroform, dried over $Na_2SO_4$ and the dried solution distilled under vacuum to give 128 grams (59.8% yield) of the ethoxylated stearic acid.

Step II: Preparation of the Bromoethanol Ester of Alpha-Ethoxylated Stearic Acid

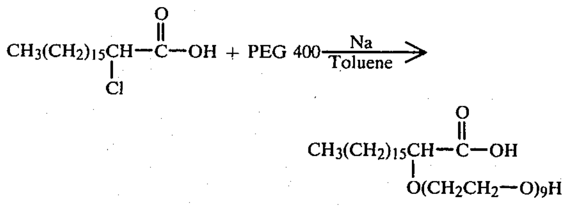

The ethoxylated stearic acid (25 g, 0.0366 moles) was dissolved in 150 ml of benzene in a 300 ml single neck, round bottom flask, equipped with a reflux condenser, water trap and mechanical stirrer. 2-Bromoethanol (45.8 g, 0.366 moles) and a catalytic amount of para-toluenesulfonic acid was added and the reaction mixture stirred at reflux until the theoretical volume of water was collected in the water trap (approximately one hour).

The reaction mixture was distilled, under reduced pressure to remove benzene and excess bromoethanol. The residue was dissolved in 400 ml of chloroform, washed neutral, and then dried over $Na_2SO_4$. The $Na_2SO_4$ was removed by filtration and the solvent removed under reduced pressure to give 26.4 g (91.3%) of a liquid product. The structure was confirmed by IR and proton nmr.

Step III: Preparation of the Choline Bromide Ester of Alpha-Ethoxylated Stearic Acid

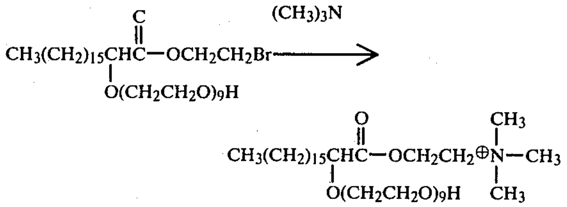

Bromoethanol ester of alpha-ethoxylated stearic acid (20 g, 0.029 moles) was dissolved in 150 ml of acetonitrile, with stirring, in a 250 ml. 3 neck, round bottom flask, eqipped with a magnetic stirrer, dry-ice/acetone condenser and gas dispersion tube. Trimethylamine was bubbled into the solution until saturated. The reaction mixture was stirred for approximately 20 hours at room temperature.

The reaction mixture was then distilled under reduced pressure to remove the solvent. The residue was then dissolved in 300 ml of chloroform, dried over $Na_2SO_4$, and then distilled under reduced pressure. The residual liquid was chilled to 0° C. and triturated with ether. The ether layers were discarded. The residue was stripped once again under vacuum to yield 17.4 g (80.1%) of a light amber liquid.

Step IV: Preparation of the Choline Ester Zwitterionic Derivative of Alpha-Ethoxylated Stearic Acid

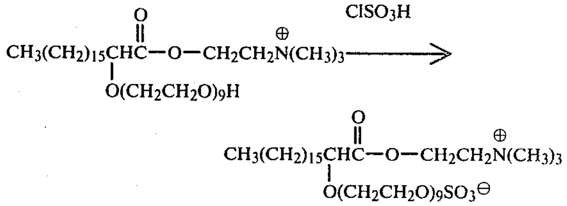

The choline bromide ester of alpha-ethoxylated stearic acid (14.8 g, 0.0172 moles) was dissolved in 200 ml of $CH_2Cl_2$ and placed in a 300 ml round bottom flask, equipped with condenser, dropping funnel, magnetic stirrer and thermometer. The solution was chilled to −10° C. in an ice-methanol bath. 4 g (0.034 moles) of chlorosulfonic acid in 5 ml of $CH_2Cl_2$ were added dropwise, maintaning a temperature below −5° C. The reaction was held at −5° C. for 30 minutes following the addition, and then left refrigerated overnight.

The chilled reaction mixture was purged with nitrogen to expel HCl gas, and then neutralized by the addition of moist $Na_2CO_3/NaHCO_3$. The mixture was dried over $Na_2SO_4$, filtered, and concentrated under vacuum to give 13.6 g (91.89%) of a viscous pale yellow liquid residue. The liquid residue was dissolved in chloroform and stirred for 6½ hours with 60 g of a mixed ion exchange resin ($H^+OH^-$). The resin suspension was filtered and the chloroform solution dried over $Na_2SO_4$ and then distilled under vacuum to give a clear yellow viscous liquid. The liquid residue was triturated with hexane and the remaining residue stripped under reduced pressure to give 7.7 g (52%) of the title compound. The compound was verified by IR, nmr and elemental analysis.

The zwitterionic surfactant compounds herein can be used in detergent compositions in an amount from about 1% to about 99% by weight of the composition. Such detergent compositions can further contain from about 1% to about 99% by weight of an organic cosurfactant selected from the group consisting of anionic, nonionic, cationic, ampholytic, and zwitterionic surfactants, and mixtures thereof; and from about 1% to about 75% by weight of a detergent builder material.

A wide range of organic detergents can be mixed, i.e. can be considered compatible with the zwitterionic compounds to form compositions useful in the present invention. In the context of this invention "compatible" is defined as causing no appreciable decrease in the ability of the alkoxylated zwitterionic compound to remove and suspend particulate soil.

Classes of compatible detergents that are expecially useful co-surfactants include the nonionic, zwitterionic, and ampholytic surfactants and fatty acid salts which can be used in a broad range of proportions to the zwitterionic compounds herein. These co-surfactants tend to increase the clay removal performance of the compounds, especially those with short alkyleneoxy chains. In contrast, most synthetic anionic detergents do not enhance the particulate soil removal performance of the zwitterionic compounds to the same extent, especially on synthetic fibers, although anionic surfactants can usefully be employed in combination with the compounds for other reasons, e.g. to obtain particularly desirable sudsing characteristics. Amongst the cationic surfactants, only those having a polyoxyalkylene function are compatible with the alkoxylated zwitterionic compounds useful in the present invention.

The ratio zwitterionic compound:co-surfactant is preferably from 10:1 to 1:10, most preferably from 4:1 to 1:10 by weight. Preferred compositions comprise from 10% to 80% of zwitterionic compound and from 90% to 20% of co-surfactant.

Suitable organic cosurfactants are those described in U.S. Pat. No. 3,929,678, Laughlin et al, issued Dec. 30, 1975, incorporated herein by reference, particularly from column 12, line 54 to column 36, line 55. Especially preferred are the nonionic surfactants, particularly those which are condensation products of aliphatic alcohols with ethylene oxide.

Suitable builder materials for use herein are those described in U.S. Pat. No. 3,925,262, Laughlin et al, issued Dec. 9, 1975, incorporated herein by reference, particularly from column 12, line 27 through column 17. Preferably, the builder represents from about 25% to 60% by weight of the detergent composition.

Optional components for use in the detergent compositions herein are those described as such in U.S. Pat. No. 3,929,678, from column 37, line 37 to column 38, line 37.

The pH of detergent formulations in accordance with the present invention can lie anywhere within the range 5-12 but is preferably chosen to fall within the range 8.0-10.5 as this provides a slight particulate soil removal benefit on synthetic fabrics. However, the use of specific optional components such as enzymes may require the selection of a product pH that will permit optimum functioning of the component concerned.

Granular formulations embodying the compositions of the present invention may be formed by any of the conventional techniques i.e., by slurrying the individual components in water and then atomizing and spray-drying the resultant mixture, or by pan or drum granulation of the components. However, it will be recognized that the ester-containing compounds herein may rapidly hydrolize under aqueous, acidic, or basic conditions, especially when subjected to high temperatures. Thus these compounds would be unstable in conventional alkaline crutcher mixing and spray-drying operations. These ester-containing compounds are preferably dry mixed or agglomerated with the other detergent components, which can conveniently be spray-dried. The stability of these compounds may also be enhanced by increasing the separation of the ester linkage from the cationic charge center of the zwitterionic compound. However, as described previously, the biodegradable linkage should not be more than ten atoms distant from the cationic charge center for ultimate biodegradation advantages over compounds known in the art.

Liquid formulations embodying the compositions of the present invention may be formed by simply admixing the components. As described above, liquid formulations containing zwitterionic compounds herein with ester linkages are preferably neutral-pH formulations. The stability of these compounds may also be enhanced by increasing the separation of the ester linkage from the cationic charge center.

Liquid detergent formulations herein may contain builders or be unbuilt. If the compositions are unbuilt, they will conventionally contain approximately 30-50% total surfactant, from 1-10% of an organic base such as mono-, di-, or tri-alkanolamine, a solubilization system such as alkali metal halide and a lower primary alcohol such as ethanol or isopropanol and approximately 30-40% water. Such compositions will normally be homogeneous single phase liquids of low viscosity (approximately 100-150 centipoises at 75° F.).

Built liquid detergent compositions may also be single phase liquids provided that the builder can be solubilized in the mixture at its level of use. Such liquids conventionally contain 10-25% total surfactant, 10-20% builder which may be organic or inorganic, 5-10% of a hydrotrope system and 50-60% of water.

Liquids of this type also have low viscosity (100-150 c.p.s. at 75° F.). Built liquid detergents incorporating components that form heterogeneous mixtures or levels of builder that cannot be completely dissolved can also embody the compositions of the present invention. Such liquids conventionally employ viscosity modifiers to produce systems having plastic shear characteristics to maintain stable dispersions and to prevent phase separation or solid settlement.

All percentages, parts, and ratios used herein are by weight unless otherwise specified.

The following nonlimiting examples illustrate the compounds and compositions of the present invention.

EXAMPLE I

Detergent compositions according to the present invention are as follows:

| | Wt. % | | | | | | | | | |
|---|---|---|---|---|---|---|---|---|---|---|
| Component | A | B | C | D | E | F | G | H | I | J |
| Compound[1] | 35.0 | 15.0 | 20.0 | 15.0 | 15.0 | 10.0 | 12.5 | 25.0 | 20.0 | 15.0 |
| $C_{12-13}(EO)6.5$[2] | | | | | 15.0 | 10.0 | 12.5 | | | 15.0 |
| $C_{14-15}(EO)7$[3] | | | | | | 10.0 | | | 20.0 | |
| Sodium $C_{12}$ linear alkylbenzene sulfonate | | | | | | | 7.5 | | | |
| Sodium aluminosilicate (hydrated zeolite A, particle diameter 1-10 microns) | | 20.0 | | 25.0 | | 15.0 | | | | |
| Sodium tripolyphosphate | | 30.0 | 50.0 | | | | 20.0 | | | |
| Sodium nitrilotriacetate | | | | | | 20.0 | | | | 5.0 |
| Sodium sulfate | | 24.0 | 25.0 | 34.0 | 30.0 | 25.0 | 25.0 | | | |
| Sodium citrate | | | | | | | | | | 15.0 |
| Sodium carbonate | 30.0 | | | 10.0 | 10.0 | | 14.0 | | | |
| Sodium silicate (2.0 ratio) | 30.0 | 5.0 | | 10.0 | 20.0 | 5.0 | 5.0 | | | |
| Ethanol | | | | | | | | | 5.7 | 5.0 |
| Triethanolamine | | | | | | | | 10.0 | 3.0 | 2.0 |
| HCl | | | | | | | | 1.2 | | |
| Enzyme[4] | | | 0.2 | | | | | | | |

-continued

| | Wt. % | | | | | | | | | |
|---|---|---|---|---|---|---|---|---|---|---|
| Component | A | B | C | D | E | F | G | H | I | J |
| Water and minors | | | | | Balance | | | | | |

[1] 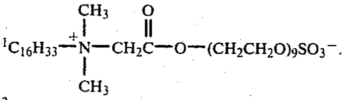

[2]Condensation product of $C_{12-13}$ alcohol with 6.5 moles of ethylene oxide, stripped to remove lower ethoxylate and nonethoxylated fractions, commercially available as Neodol 23-6.5T, from Shell Chemical Corporation.
[3]Condensation product of $C_{14-15}$ alcohol with 7 moles of ethylene oxide, commercially available as Neodol 45-7 from Shell Chemical Corporation.
[4]Proteolytic enzyme from *Thermoactinomyces vulgaris* ATCC15734.

Compositions A-G above are granular detergent compositions prepared by dry mixing Compound 1 with solid detergent granules comprising the other ingredients. The solid granules are prepared by first dissolving all ingredients in water to provide a substantially homogeneous crutcher mix, and then spray-drying the crutcher mix in standard fashion. Composition C is highly-built detergent composition containing a proteolytic enzyme and especially adapted for use under European washing conditions. It is prepared in the same manner as Compositions A, B, and D-G, with the exception that the enzyme is not passed through the crutcher mix or spray-drying tower, but is added to the detergent granules after spray-drying is complete in order to maintain enzyme activity.

Compositions H, I and J are liquid detergent compositions prepared by simply mixing the components in the indicated proportions. It is preferred that the components be dissolved in aqueous ethanol solutions having a 9:1 water:ethanol ratio.

The above compositions are added (1¼ cups for granular compositions, ¼ cup for liquid compositions) to a standard top-loading automatic washing machine containing 25 gallons of water. A load of mixed fabrics is laundered in the resulting liquor using the machine manufacturer's instructions. After rinsing and drying, the fabrics are found to be substantially free from heavy clay soil stains originally present thereon. The clay soil removal performance of the composition is fully equivalent to, or substantially better than, that of commercially available, built laundry detergents. The Composition C is used in a front-loading washing machine typical of that used in Germany. The composition is used at a concentration of about 250 ppm of the laundering liquor. Cleaning of fabrics heavily soiled with clay is equivalent to, or substantially better than, that secured with well-known commercial detergents. This composition is exceptionally useful as a laundry pre-soak to assist in the removal of clay, lipid and proteinaceous (e.g., blood stains) soils from fabrics. Compositions H, I and J are particularly desirable as spot-cleaning compositions when directly applied to heavily soiled fabrics prior to their laundering in an automatic washing machine.

Substantially similar cleaning is obtained when Compound 1 in the above compositions is replaced with any zwitterionic surfactant compound of the formula

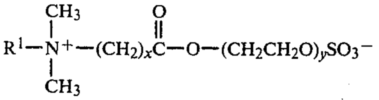

wherein $R^1$ is a $C_{14}$–$C_{20}$ alkyl group, x is 1 or an integer from 3 to 5, and y is anywhere from 6 to 12. Substantially similar results are obtained when, in the above compounds, the

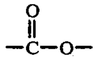

group is replaced with

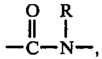, or with

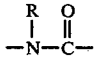 and 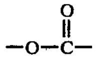

when x is an integer from 2 to 5.

Substantially similar cleaning of fabrics is obtained when the above zwitterionic surfactant compounds are replaced with one of the formula

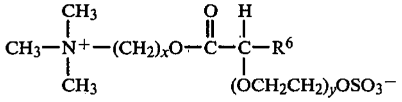

wherein $R^6$ is a $C_{14}$–$C_{20}$ alkyl group, x is an integer from 2 to 5 and y is from 6 to 12. Comparable results are also obtained when the

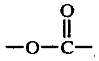

group is replaced with

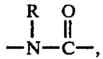, or with

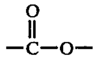 and 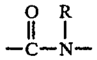

when x is 1 or an integer from 3 to 5.

EXAMPLE II

The biodegradation advantage of the compounds of the present invention is shown by a comparison of the biodegradability (expressed as % $TCO_2$) of certain zwitterionic compounds, having a chemically labile linkage between their cationic and anionic charge centers (Group A), with other zwitterionic compounds either having no such linkage or having a linkage not located between the charge centers (both Group B). The biodegradation screening test is based on the proposition that, as a carbonaceous material is acted upon by aerobic bacteria capable of utilizing it as a carbon and energy source, the molecule will be converted to cellular material, carbon dioxide and water. The ultimate biodegradability of a given material may then be estimated by measuring the amount of $CO_2$ produced or the amount of $O_2$ consumed by acclimated bacteria during a given time, and relating these figures to calculated theoretical yield based on the structure and molecular weight of the compound under investigation. This test is more fully described in the published article "Biodegradability of Nonionic Surfactants: Screening Test for Predicting Rate and Ultimate Biodegradation", Sturm, Journal of the American Oil Chemists' Society, Vol. 50, No. 5, pages 159-167 (1973), which is incorporated herein by reference.

The results were as follows:

| Compound | Test Concentration (mg/l) | Results (% $TCO_2$) |
|---|---|---|
| | Group A | |
| 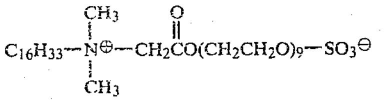 | 11<br>11<br>10<br>10<br>10<br>10<br>10 | 81% (26 days)<br>89% (40 days)<br>72% (26 days)<br>57% (26 days)<br>80% (26 days)<br>81% (26 days)<br>78% (26 days) |
| 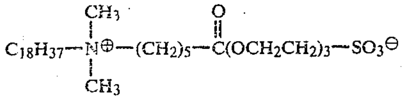 | 20<br>20<br>20<br>10<br>10 | 55% (26 days)<br>33% (26 days)<br>44% (40 days)<br>50% (26 days)<br>64% (40 days) |
| | Group B | |
| 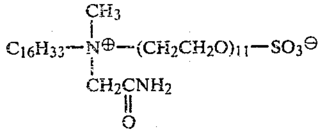 | 11<br>11 | 34% (26 days)<br>39% (40 days) |
| 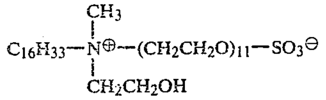 | 10<br>10 | 30% (26 days)<br>36% (40 days) |
| 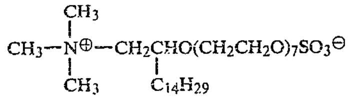 | 10<br>10 | 27% (26 days)<br>30% (40 days) |
| 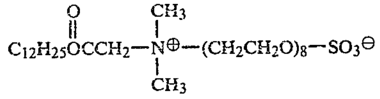 | 10<br>10 | 33% (26 days)<br>34% (40 days) |
| 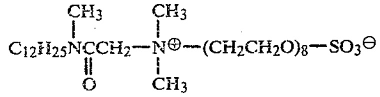 | 10<br>10 | 22% (26 days)<br>23% (40 days) |
| 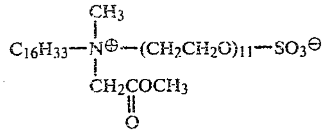 | 10<br>10 | 34% (26 days)<br>37% (40 days) |
| 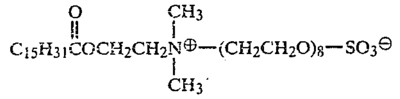 | 20 | 37% (26 days) |
| 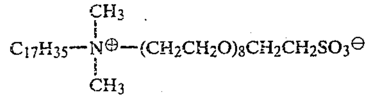 | 20 | 24% (26 days) |
| 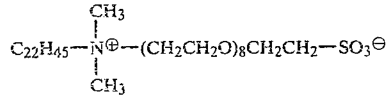 | 20 | 39% (26 days) |
| 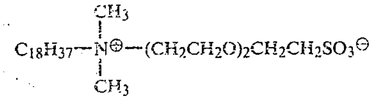 | 20 | 46% (26 days) |

-continued

| Compound | Test Concentration (mg/l) | Results (% $TCO_2$) |
|---|---|---|
| 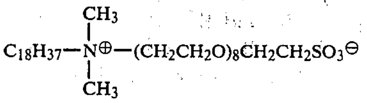 | 20 | 28% (26 days) |
| 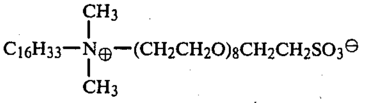 | 20 | 22% (26 days) |
| 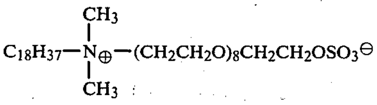 | 20 | 2% (26 days) |
| | 20 | 3% (26 days) |
| | 10 | −2% (26 days) |
| | 10 | 4% (26 days) |
| 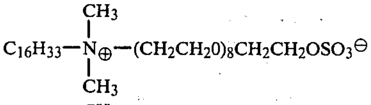 | 20 | 30% (26 days) |
| | 10 | 17% (26 days) |
| | 10 | 25% (26 days) |
| 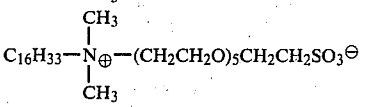 | 20 | 33% (26 days) |
| 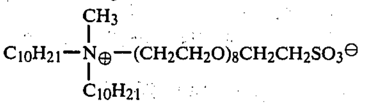 | 20 | 7% (26 days) |

EXAMPLE III

The clay removal performance provided by a compound of the present invention (Compound A) was compared with that provided by a fully-built phosphate detergent formulation (Control) according to the following procedure.

Clay removal comparisons were conducted in standard 1 liter Tergotometers employing water of 7 grain hardness (3:1 $Ca^{++}$:$Mg^{++}$) and a temperature of 105° F. Soiled swatches were washed in the Tergotometer for 10 minutes and rinsed twice with water at 80° F. and 7 grain hardness for 2 minutes.

Three types of fabrics were employed as swatches: cotton; 65% polyester 35% cotton blend; and 100% Dacron ® polyester knit. The swatches were 2¾ inches by 2¾ inches in size and were soiled by dipping in an aqueous slurry of local clay and subsequently baked to remove the water. The dipping and baking were repeated three, four and two times for cotton, cotton/polyester and polyester, respectively. Three swatches of each fabric type were employed, for a total of 9 swatches for each test wash in the Tergotometer.

One wash employed only 250 ppm of Compound A. Another wash used 1000 ppm (total detergent composition) of the Control composition built with 50% sodium tripolyphosphate. Neither composition contained optical brighteners. The product washes approximated a conventional home use laundry situation. After laundering, the swatches were dried in a mini-dryer with one clean, desized terry cloth added for bulk adjustment.

The swatches were graded before and after washing on a Gardner Whiteness meter reading the L,a, and b coordinates. Whiteness (W) was calculated as:

$$W = \frac{7L^2 - 40Lb}{700}$$

The clay removal performance of each detergent composition was determined by finding the difference in whiteness (ΔW) before and after washing as:

$$\Delta W = W_{after} - W_{before}$$

The performance provided by Compound A ($\Delta W_A$) was expressed as a percentage of that provided by the Control composition ($\Delta W_{control}$). The results are as follows:

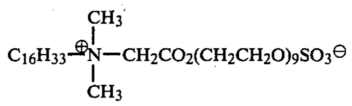

Compound A

| Control Component | Wt. % |
|---|---|
| Sodium $C_{12}$ alkylbenzene sulphonate | 7.55 |
| Sodium tallow alkyl sulphate | 9.25 |
| Coconut alcohol + 6 mole EO | 0.60 |
| Diethanolamide | 1.60 |
| Sodium tripolyphosphate | 50.00 |
| Sodium silicate solids | 5.90 |
| Sodium sulphate | 14.20 |
| Moisture | 10.00 |
| Miscellaneous | 0.30 |
| | 100.00 |

| % Performance of Control at 1000 ppm Provided by 250 ppm Compound A | | |
|---|---|---|
| Cotton | Polycotton | Polyester |
| 102 | 93 | 101 |

What is claimed is:

1. A compound of the formula

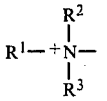

wherein $R^1$ is selected from the group consisting of straight chain, branched chain or cyclic $C_1$–$C_{30}$ alkyl, hydroxyalkyl, alkenyl and hydroxyalkenyl moieties and alkaryl moieties in which the alkyl group has 6–24 carbon atoms; $R^2$ and $R^3$ are each selected from the group consisting of straight chain, branched chain or cyclic $C_1$–$C_{30}$ alkyl, hydroxyalkyl, alkenyl and hydroxyalkenyl moieties, alkaryl moieties in which the alkyl group has 6–24 carbon atoms, and $C_2$–$C_4$ alkylene oxide having from 1 to 5 alkyleneoxy units; $R^4$ is an alkylene, hydroxyalkylene, alkylene oxide, alkenylene, arylene, or alkarylene group, provided that A is no more than 10 atoms from M; each A is the cationic charge center

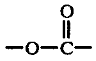 or 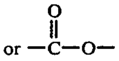

m is 1 or 2, but can only be 2 when an additional $R^5$ group separates the A structures; $R^5$ is a $C_1$–$C_{10}$ alkylene, hydroxyalkylene, alkenylene, arylene, or alkarylene group; each n is independently 0 or 1; $R^6$ is selected from the group consisting of straight chain, branched chain or cyclic $C_1$–$C_{30}$ alkyl, hydroxyalkyl, alkenyl and hydroxyalkenyl moieties and alkaryl moieties in which the alkyl group has 6–24 carbon atoms; $R^7$ is a $C_2$–$C_4$ alkylene group or mixtures thereof; y is from 3 to 100; and X is sulfate, sulfonate or carboxylate; provided that the above groups are selected such that $R^1$, $R^2$, $R^3$ and $R^6$, together, contain from 12 to 50 carbon atoms and no peroxy linkages are present in the compound.

2. A compound according to claim 1 wherein m is 1.

3. A compound according to claim 1 wherein $R^7$ is an ethylene group.

4. A compound according to claim 3 wherein y is from 3 to 30.

5. A compound according to claim 4 wherein y is from 6 to 12.

6. A compound according to claim 1 wherein $R^1$, $R^2$, $R^3$ and $R^6$, together, contain from 15 to 30 carbon atoms.

7. A compound according to claim 1 wherein A is located from the second to the sixth atom distant from the cationic charge center.

8. A compound according to claim 1 wherein m is 1, $R^7$ is an ethylene group and y is from 3 to 30.

9. A compound according to claim 8 wherein the n subscript for the ($CHR^6$) group is zero, $R^1$ is a straight chain or branched chain $C_{10}$–$C_{30}$ alkyl or alkenyl moiety, or an alkaryl moiety having $C_6$–$C_{24}$ alkyl group, and $R^2$ and $R^3$ are each independently selected from $C_1$–$C_4$ alkyl or alkenyl moieties or hydroxy-substituted $C_1$–$C_4$ alkyl or alkenyl moieties.

10. A compound according to claim 9 wherein $R^1$ is a $C_{14}$–$C_{22}$ alkyl moiety or alkaryl moiety having a $C_8$–$C_{16}$ alkyl group and $R^2$ and $R^3$ are each independently selected from $C_1$–$C_3$ alkyl moieties.

11. A compound according to claim 10 having the formula

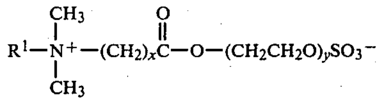

wherein $R^1$ is a $C_{14}$–$C_{20}$ alkyl group, x is 1 or an integer from 3 to 5 and y is from 6 to 12.

12. A compound according to claim 11 wherein $R^1$ is a $C_{16}$ alkyl group, x is 1 and y is 9.

13. A compound according to claim 8 wherein n subscript for the ($CHR^6$) group is 1, $R^6$ is straight chain or branched chain $C_{10}$–$C_{30}$ alkyl or alkenyl moiety or an alkaryl moiety having a $C_6$–$C_{25}$ alkyl group, and $R^1$, $R^2$ and $R^3$ are each independently selected from $C_1$–$C_4$ alkyl, alkenyl, or hydroxy-substituted alkyl or alkenyl moieties.

14. A compound according to claim 13 wherein $R^6$ is a $C_{14}$–$C_{22}$ alkyl moiety or alkaryl moiety having a $C_8$–$C_{16}$ alkyl group and $R^1$, $R^2$ and $R^3$ are each independently selected from $C_1$–$C_3$ alkyl moieties.

15. A compound according to claim 14 having the formula

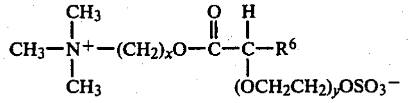

wherein $R^6$ is a $C_{14}$–$C_{20}$ alkyl group, x is an integer from 2 to 5 and y is from 6 to 12.

16. A compound according to claim 15 wherein $R^6$ is a $C_{16}$ alkyl group, x is 2 and y is 9.

17. A detergent composition comprising from about 1% to about 99% by weight of a compound according to claim 1.

18. A detergent composition according to claim 17 further comprising from about 1% to about 99% by weight of an organic cosurfactant selected from the group consisting of anionic, nonionic, cationic, ampholytic, and zwitterionic surfactants, and mixtures thereof.

19. A detergent composition according to claim 17 or 18 further comprising from about 1% to about 75% by weight of a detergent builder material.

* * * * *

UNITED STATES PATENT AND TRADEMARK OFFICE
CERTIFICATE OF CORRECTION

PATENT NO. : 4,301,044

DATED : November 17, 1981

INVENTOR(S) : G. E. Wentler, J. McGrady, E. P. Gosselink, W. A. Cilley

It is certified that error appears in the above-identified patent and that said Letters Patent are hereby corrected as shown below:

Formula at top of column 19 should be:

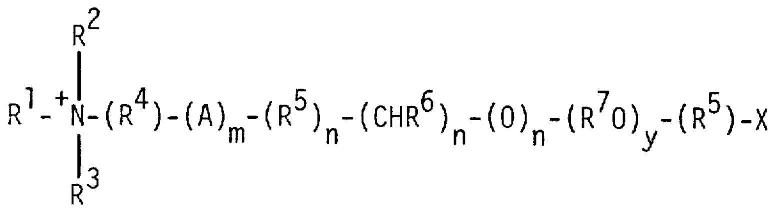

Line 20 of Claim 1 should read -- atoms from the cationic charge center; each A is --

Signed and Sealed this

*Twenth-eighth* Day of *September 1982*

[SEAL]

*Attest:*

GERALD J. MOSSINGHOFF

*Attesting Officer* *Commissioner of Patents and Trademarks*